United States Patent [19]  
Kershaw

[11] 4,147,717  
[45] Apr. 3, 1979

[54] PROCESS FOR PURIFYING ADIPONITRILE

[75] Inventor: Bernard J. Kershaw, Kingston, Canada

[73] Assignee: Du Pont of Canada Limited, Montreal, Canada

[21] Appl. No.: 858,663

[22] Filed: Dec. 8, 1977

Related U.S. Application Data

[63] Continuation-in-part of Ser. No. 717,909, Aug. 26, 1976, abandoned.

[51] Int. Cl.$^2$ ............................................. C07C 121/26
[52] U.S. Cl. .......................... 260/465.8 R; 260/465.2
[58] Field of Search ..................... 260/465.8 R, 583 K, 260/583 P, 465.2

[56] References Cited

PUBLICATIONS

Pickert et al., Chemical Engineering, Jul. 29, 1968, pp. 133–142.
Union Carbide bulletin—"A Report on Molecular Sieve Catalysts", 5 pp.
Union Carbide bulletin—"A Report on Molecular Sieve Catalyst SK-500", 8 pp.

Primary Examiner—Joseph Paul Brust

[57] ABSTRACT

Certain basic impurities, e.g., N-heterocyclic amines such as 2-methyl-4-amino-5,6-trimethylene pyrimidine are removed from adiponitrile by contact with solid acidic sorption agents, e.g., weak cation exchange resins before its hydrogenation to hexamethylene diamine to reduce odor and color of products prepared from the diamine.

6 Claims, No Drawings

PROCESS FOR PURIFYING ADIPONITRILE

CROSS-REFERENCE TO RELATED APPLICATIONS

This application is a continuation-in-part of my copending application Ser. No. 717,909 filed on Aug. 26, 1976 now abandoned.

BACKGROUND OF THE INVENTION

1. Field of the Invention

The present invention relates to the treatment of adiponitrile and in particular to a process for reducing the amount of basic impurities in crude adiponitrile especially adiponitrile obtained from adipic acid and ammonia.

2. Description of the Prior Art

Adiponitrile obtained from adipic acid contains impurities, some of which boil at temperatures close to the boiling point of adiponitrile. 2-Cyanocyclopentylideneimine, (CPI), is an example of such an impurity. Close boiling impurities frequently cannot be removed efficiently in industrial scale distillation columns and lead to impurities in subsequent derivatives, in particular in hexamethylene diamine, that are difficult to remove. Failure to remove these latter impurities may result in inferior and variable properties, especially in polymers manufactured using such impure hexamethylene diamine. Some techniques for the purification of adiponitrile are known in the art. For example, adiponitrile may be treated with a solid acidic catalyst in the presence of water and at a temperature of at least 140° C. to remove 2-cyanocyclopentylideneimine from the adiponitrile as described in Canadian Pat. No. 912,036 of B. J. Kershaw, issued Oct. 10, 1972.

SUMMARY OF THE INVENTION

A process for reducing the level of N-heterocyclic amines in adiponitrile by contacting said adiponitrile with a solid acidic sorption agent while minimizing the hydrolysis of any 2-cyanocyclopentylideneimine present in the adiponitrile, said sorption agent being selected from the class consisting of (1) weak acid cation exchange resins, (2) boron phosphate (3) bentonite (4) molecular sieves and (5) mixtures of the foregoing with said process being conducted essentially in the absence of water when molecular sieves comprise said sorption agent.

The adiponitrile so treated can be hydrogenated in the supercritical vapor phase to produce hexamethylene diamine. The hydrogenation is carried out at a temperature within the range 100° to 200° C. under superatmospheric pressures in the presence of ammonia and a catalyst comprising an iron compound in granular form which has been activated by contact with hydrogen at temperatures not exceeding 600° C., and yields a product preferably containing less than 1 part per million of 2-methyl-5,6-trimethylene pyrimidine (MHP).

It is preferred to contact the adiponitrile with weak-acid cation exchange resins, boron phosphate and bentonite in the presence of water (1–10% by weight based upon the weight of the adiponitrile) at temperatures of 20°–140° C., 20°–100° C. and 20°–100° C., respectively.

DETAILED DESCRIPTION OF THE INVENTION

Adiponitrile can be obtained by reacting adipic acid with ammonia in the presence of a dehydrating catalyst, for example, by the techniques disclosed in U.S. Pat. Nos. 2,200,734 and 2,273,633. Such adiponitrile contains impurities which boil at temperatures close to the boiling point of adiponitrile, e.g., 2-cyanocyclopentylideneimine (CPI). These close boiling impurities are not removed efficiently in industrial scale distillation columns and form impurities in subsequent derivatives, e.g., in hexamethylene diamine, that are difficult to remove and result in inferior and variable properties in polymers made from the diamine. Impurities in the form of cyclic amines, especially N-heterocyclic amines are especially troublesome. Examples of such impurities are 2-methyl-4-amino-5,6-trimethylene pyrimidine (MAP), 2-amine-3,4,5,6-bis(trimethylene) pyridine (ABP), and 2-cyclopentyl-4-amino-5,6-trimethylene pyrimidine (VAP).

When adiponitrile containing the above-discussed impurities is hydrogenated as described by J. R. B. Boocock, F. T. Flood and B. J. Kershaw in Canadian Pat. No. 907,059 which issued on Aug. 8, 1972 and Canadian Pat. No. 915,707 which issued Nov. 28, 1972 to B. J. Kershaw, M. G. Pounder and K. R. Wilkins, odoriferous compounds are formed from the N-heterocyclic compounds, especially MAP. There is a need for an improved process for the manufacture of hexamethylene diamine by the hydrogenation of adiponitrile, using iron catalyst, in which the formation of odoriferous compounds is reduced.

It has now been discovered that the above-described impurities can be removed, or at least substantially reduced, by contacting the adiponitrile with certain solid acidic sorption agents.

The crude adiponitrile being treated so as to reduce the level of N-heterocyclic amines therein should be essentially free of ammonia and should be treated under conditions which minimize the formation of ammonia, e.g., by hydrolysis of CPI since ammonia causes less efficient removal of the N-heterocyclic amines and/or decreased capacity of the agent used for the removal of the amines.

The solid acidic sorption agent should be capable of being separated from the adiponitrile after treatment and should not cause deleterious effects in the adiponitrile, for example, by the introduction of significant amounts of impurities, and/or in the hydrogenation of the treated adiponitrile with iron catalyst. The process conditions used in the treatment of the adiponitrile, e.g., temperature, pressure, will depend on the agent with which the adiponitrile is treated, examples of such conditions being discussed hereinafter. In addition, the adiponitrile should be treated under conditions, e.g., of temperature, that prevent significant loss of adiponitrile by, for example, degradation or hydrolysis. The adiponitrile may be treated in the presence or absence of water, depending on the agent used in the treatment step.

In the first step of the process, adiponitrile is treated with the agent in a continuous process or in a batch process. Preferably, the adiponitrile is continuously passed through a fixed bed of the agent.

While the adiponitrile treated so as to reduce the amount of N-heterocyclic amines therein is described as "crude adiponitrile", the adiponitrile being treated is preferably adiponitrile that has been subjected to partial purification, e.g., by distillation.

The crude adiponitrile may be treated by a variety of techniques in order to reduce the amount of N-heterocyclic amines therein. For example, the adiponitrile (substantially free of ammonia) may be treated with a weak-acid cation exchange resin, in its hydrogen form, in the presence of water at a temperature in the range from 20° C. up to the temperature at which degradation of the weak-acid cation exchange resin becomes significant. Preferred temperatures are in the range of 20° C. to 140° C. and especially in the range of 25° C. to 100° C. Preferably the adiponitrile contains at least 5%, especially 5–10%, by weight of water although the water content in the adiponitrile may be varied from about 1% by weight to a ratio of water to adiponitrile of about 2:1 on a weight basis, the upper limit of water being determined primarily by practical considerations. The treatment of adiponitrile with a weak-acid cation exchange resin in the presence of water results in essentially no hydrolysis of 2-cyanocyclopentylideneimine. Such hydrolysis forms ammonia, which is adsorbed by the resin thereby reducing its capacity for removing other amines.

The amines are removed from the weak-acid cation exchange resin by contacting the resin at ambient temperatures with a strong acid, for example, hydrochloric or sulphuric acid, in excess of the stoichiometric amount of acid required to convert the resin to its acid or hydrogen form. The resin is used in the process of the present invention in its acid or hydrogen form. The relatively low amount of acid required for regeneration of weak-acid cation exchange resins, as compared with strong-acid cation exchange resins, may have advantages with respect to the control of pollution from the process.

Another method for the treatment of crude adiponitrile uses a molecular sieve selected from the group consisting of Type X and Type Y, and mixtures thereof, essentially in the absence of water at a temperature in the range of 100° C. to 250° C. Type Y molecular sieves are preferred. The molecular sieve may be in a polyvalent cation form, the ammonia form or the hydrogen form. The expression "treatment of adiponitrile essentially in the absence of water" means the treatment of adiponitrile containing less than 0.1% water. If the adiponitrile contains water and, in addition, contains 2-cyanocyclopentylideneimine as an impurity the 2-cyanocyclopentylideneimine may be hydrolyzed, one product of the hydrolysis being ammonia.

Molecular sieves, which are also referred to as zeolites, are aluminosilicates having a framework structure with cavities capable of being occupied by large ions and water molecules. Molecular sieves may be used as catalysts, as ion exchange materials or as absorbent materials. There are many types of molecular sieves and their properties depend on, for example, the framework structure of the aluminosilicate and the resultant pore size, the silica/alumina ratio and the type of cation in the structure. Examples of molecular sieves of relatively large pore size are Types X and Y, both of which are structurally related to the mineral faujasite, $(Na_2, Ca, Mg)_{60} (AlO_2)_{60} (SiO_2)_{132} \cdot 26OH_2O$. Type Y has a higher silica/alumina ratio than Type X. Type X molecular sieves have been disclosed in U.S. Pat. No. 2,882,244 of R. M. Milton which issued Apr. 14, 1959 and Type Y molecular sieves have been disclosed in U.S. Pat. No. 3,130,007 of D. W. Breck which issued Apr. 21, 1964. The basic crystal structures of Type X and Type Y molecular sieves may be identified by X-ray diffraction. Type X and Type Y molecular sieves are available in many forms, e.g., with univalent cations, for example, sodium, ammonia, hydrogen and with multivalent cations, for example, calcium, magnesium, nickel. As is disclosed in the aforementioned U.S. Pat. No. 3,130,007 molecular sieves are generally synthesized in the sodium form and other types are derived therefrom. Molecular sieves are discussed in greater detail in "Molecular Sieve Zeolites: Trendsetters in Heterogeneous Catalysis" by P. E. Pickert et al. in Chemical Engineering, July 29, 1968, pages 2–11 and in bulletins on LINDE® molecular sieves obtainable from the Linde Division of Union Carbide Corporation, for example, bulletins entitled "A Report on Molecular Sieve Catalysts" and "A Report on Molecular Sieve Catalyst SK-500".

A number of techniques for regeneration of molecular sieves may be used. For example, the molecular sieve may be treated with a solution of ammonia at temperatures of from ambient to about 70° C. followed by a heat treatment of the molecular sieve to remove ammonia. Alternatively the molecular sieve may be heated under an inert gas, treated with steam at high temperatures or treated with a base of higher affinity for the molecular sieve that the amines followed by treatment to remove the base.

A further method for the treatment of crude adiponitrile uses boron phosphate and/or bentonite at a temperature in the range 20° C. to 100° C. and, preferably, substantially in the absence of ammonia which is preferentially absorbed on the boron phosphate and/or bentonite. The adiponitrile may be treated in the presence or absence of water. However, it is preferred to treat the adiponitrile in the presence of both water and a water-soluble acidic compound, for example, acetic acid or phosphoric acid. The adiponitrile may contain up to two parts, by weight, of water per part of adiponitrile, but preferably contains 1 to 10% by weight of water.

Boron phosphate or bentonite is regenerated by heating under an atmosphere of inert gas by treating with steam at high temperatures or by treating with a base of higher affinity for the boron phosphate or bentonite followed by treatment to remove the base. For example, the boron phosphate or bentonite may be contacted with an ammonia solution at a temperature of from ambient to about 70° C., separated therefrom and heated to remove ammonia.

The pressure used in the treatment of the adiponitrile to remove the amines is not critical. The pressure will depend primarily on other process variables, for example, the temperature at which the treatment process is operated.

After treatment to reduce the level of N-heterocyclic amines therein the adiponitrile is hydrogenated in supercritical vapor phase to produce hexamethylene diamine. The hydrogenation is carried out at temperatures in the range 100° C. to 200° C. under superatmospheric pressures in the presence of ammonia and a catalyst. The catalyst comprises an iron compound in granular form which has been activated by contact with hydrogen at temperatures not exceeding 600° C., the iron compound being capable ultimately of conversion into elemental iron. By "super-critical vapor phase" is meant a condition in which the temperature of the reactor is above the pseudo-critical temperature of the reactor feed mixture.

When the iron catalyst is used in a fixed bed it is preferably used in relatively coarse granular form, e.g., a particle size of from about 0.25 to 0.50 cm. Much finer particle sizes tending to powders may be used in a fluid bed or in a slurry-type reactor.

The preferred method of activation of the iron catalyst is to treat iron oxide by heating it at about 400° C. in a furnace under a stream of dry hydrogen for 40 to 50 hours using a relatively high flow rate for the stream of hydrogen. If activation is allowed to proceed for too long a period, sintering of the catalyst may occur. It is desirable that substantially no water be present during the activation treatment. The catalyst prepared in this manner will frequently show surface areas of up to 30–35 m$^2$/g. The activation of iron catalysts is described in greater detail in the aforementioned Canadian Pat. No. 907,059 of Boocock et al.

The hydrogenation step of the process of the present invention is particularly adapted for continuous operation. The temperature of the hydrogenation should be regulated within the range of from 100° C. to 200° C. and accurately maintained during the continuous reaction by conventional procedures such as the regulation of flow rates and the temperature of the reactants. Temperatures of 105° C. to 165° C. especially 110° C. to 150° C. are preferred. The hexamethylene diamine formed on hydrogenation of adiponitrile should contain less than 1 ppm of MHP.

The following examples are presented to illustrate, but not to restrict the present invention.

EXAMPLE I

A sample of 100 ml of adiponitrile obtained from adipic acid and ammonia (#1) was heated to 95° C. 2 g of SK-500 ® (polyvalent cation form), a Type Y molecular sieve obtainable from the Linde Division of Union Carbide Corporation, were added to the adiponitrile and the resultant mixture was stirred for 2 hours at 95° C. The molecular sieve was filtered off and the filtrate of purified adiponitrile, referred to hereinafter as adiponitrile #2, was analyzed by gas chromatographic techniques.

The results of the analysis are given in Table I.

EXAMPLE II

A sample of 100 ml of adiponitrile #1 was mixed with 6 ml of water and 2 g of DUOLITE ® CC-3, a weak-acid cation exchange resin obtainable from Diamond Shamrock Chemical Company. The mixture was stirred for one hour at ambient temperature and then filtered. The filtrate of adiponitrile was partially dehydrated by heating to 160° C. under reduced pressure (12 mm Hg). The dehydrated adiponitrile, hereinafter referred to as adiponitrile #3, was analyzed using gas chromatographic techniques.

Approximately 28 g of −8+14 mesh sample of a naturally occurring iron oxide (Fe$_2$O$_3$) containing a few percent of silica and other trace impurities was activated by heating in a stream of hydrogen (16 l/hr) and nitrogen (2.4 l/hr) at a temperature of 300°–350° C. until essentially all of the iron oxide has been converted to elemental iron.

2 g of adiponitrile, 1 g of the activated iron catalyst and 20 g of anhydrous ammonia were added to a stainless steel autoclave having a capacity of 100 ml. The autoclave was then pressurized to about 90 kg/cm$^2$ with hydrogen. The autoclave was then heated to 180° C. and maintained at 180° C. for 30 minutes. The autoclave was continuously agitated during this period at elevated temperature. After cooling the product obtained was dissolved in a minimum amount of water and analyzed for MHP using gas chromatographic techniques. Further experimental details and the results obtained are given in Table II.

TABLE I

| Adiponitrile | 1 | 2 | 3 |
|---|---|---|---|
| Impurities (%) | | | |
| CPI | 0.175 | 0.158 | 0.191 |
| Succinimide | 0.080 | 0.038 | 0.090 |
| MAP | 0.026 | 0.0045 | 0.0065 |
| ABP | 0.104 | 0.033 | 0.016 |
| CVA | 0.092 | 0.069 | 0.099 |
| VAP | 0.0076 | 0.0051 | 0.0035 |
| Water | 0.060 | 0.090 | 0.010 |

N.B. all analyses expressed as percentages on a weight volume basis, remaining component essentially adiponitrile.

TABLE II

| Run No. | 1 | 2 | 3 | 4 | 5 |
|---|---|---|---|---|---|
| Adiponitrile # | 1 | 1 | 1 | 2 | 3 |
| Autoclave Pressure (kg/cm$^2$) | 224 | 249 | 214 | 240 | 238 |
| MHP (%) | 0.0011 | 0.0011 | 0.0010 | 0.0001 | 0.0000 |
| Odor | yes | yes | yes | yes | no |

Adiponitrile #1, ammonia and hydrogen were fed to a continuous reactor that was 2.5 cm in diameter and 35 cm in length and which contain an activated fused iron oxide containing 3% of alumina. The hexamethylene diamine obtained was analyzed using gas chromatographic techniques. Further experimental details and the results obtained are given in Table III.

As a comparison the iron catalyst was replaced with a cobalt catalyst of the type described as cobalt catalyst (X) in Canadian Pat. No. 915,707. Experimental details and the results obtained are given in Table III.

The results show that under similar conditions the hydrogenation of adiponitrile using an iron catalyst results in the formation of the odorous compound MHP whereas with a cobalt catalyst MHP is not formed.

TABLE III

| Run No. | 1 | 2 | 3 | 4 |
|---|---|---|---|---|
| Catalyst | Fe | Fe | Co | Co |
| Adiponitrile (g/hr.) | 399 | 470 | 448 | 484 |
| Ammonia (g/hr.) | 1780 | 2200 | 1800 | 2080 |
| Hydrogen (l/min.) | 27.4 | 39.2 | 36.8 | 37.8 |
| Reactor Temperature(° C.) | | | | |
| Inlet | 110 | 104 | 88 | 95 |
| Outlet | 155 | 144 | 132 | 136 |
| Hexamethylene Diamine, yield (%) | 97.0 | 97.8 | 96.8 | 96.6 |
| MHP in Hexamethylene Diamine (%) | 0.0019 | 0.0011 | 0.000 | 0.000 |

Note:
Adiponitrile #1 had not been treated so as to reduce the amount of N-heterocyclic amines therein.

EXAMPLE III

To 50 ml of crude adiponitrile referred to hereinafter as adiponitrile #4, the composition of which is given in Table IV hereinafter, were added 3 ml of water and 2 g of DUOLITE ® CC-33, a weak-acid cation exchange resin obtainable from Diamond Shamrock Chemical Company. The resulting mixture was stirred for 30 minutes at ambient temperature and then filtered. The filtrate of treated adiponitrile so obtained was analyzed by gas chromatography. The results were as follows:

| Component | Before Treatment* With Resin (%) | After Treatment With Resin (%) | Removal of Impurity (%) |
|---|---|---|---|
| MAP | 0.040 | 0.0079 | 80 |
| ABP | 0.071 | 0.019 | 75 |
| CPI | 0.35 | 0.35 | 0 |

*Analyses are on a solution basis, i.e., adiponitrile plus water.

Example III was repeated except that no water was added to the adiponitrile. The results were as follows:

| Impurity | Before Treatment With Resin (%) | After Treatment With Resin (%) | Removal of Impurity (%) |
|---|---|---|---|
| MAP | 0.040 | 0.038 | 5 |

EXAMPLE IV

To 50 ml of a crude adiponitrile referred to hereinafter as adiponitrile #5, the composition of which is given in Table IV hereinafter, were added water and DUOLITE® CC-3 weak-acid cation exchange resin. The resulting mixture was stirred for 30 minutes and a sample of the adiponitrile was analyzed by gas chromatography. A further analysis was made after a total of 60 minutes treatment. The results for a series of runs are given in Table V.

The hydrolysis product of CPI, 2-cyanocyclopentanone, was not detected in any of the samples.

EXAMPLE V

Approximately 37 g of DUOLITE® CC-3 weak-acid cation exchange resin were placed in a glass column of approximately 2.5 cm internal diameter. 60 l ml of water were mixed with one liter of adiponitrile #4 and the resulting solution was passed down through the glass column. The contact time of adiponitrile with the cation exchange resin was approximately 2.5 minutes. Samples of the treated adiponitrile eluting from the glass column were taken periodically and analyzed by gas chromatography. The results were as follows:

| Sample* | MAP(%) | Removal of MAP (%) | ABP (%) | Removal of ABP (%) |
|---|---|---|---|---|
| Treated #1 | 0.0055 | 86 | 0.012 | 83 |
| Treated #2 | 0.0085 | 79 | 0.012 | 83 |
| Treated #3 | 0.015 | 63 | 0.023 | 68 |

*Treated #1 — after 100 ml of treated mixture had eluted from the column, the next 100 ml was collected and this sample taken therefrom
Treated #2 — after 400 ml of treated mixture had eluted from the column, the next 200 ml was collected and this sample taken therefrom.
Treated #3 — sample taken from the final 70 ml eluted from the column.

After treatment of the adiponitrile the cation exchange resin in the column was treated with 40 ml of 15% hydrochloric acid and then washed with distilled water until the eluent was free of acid. A solution of 30 ml of water in 500 ml of adiponitrile #4 was then passed down through the cation exchange resin as described above. The results were:

| Sample* | MAP (%) | Removal of MAP(%) | ABP (%) | Removal of ABP (%) |
|---|---|---|---|---|
| Treated #1 | 0.0026 | 94 | 0.023 | 67 |
| Treated #2 | 0.0063 | 84 | 0.022 | 69 |
| Treated #3 | 0.0078 | 81 | 0.025 | 65 |

*Treated #1 — sample taken from first 100 ml of eluent.
Treated #2 — after 100 ml of treated mixture had eluted from the column, the next 300 ml was collected and this sample taken therefrom.
Treated #3 — sample taken from the last 100 ml of eluent.

TABLE IV*

| Component | Adiponitrile #4 | Adiponitrile #5 | Adiponitrile #6 |
|---|---|---|---|
| MAP | 0.042 | 0.028 | |
| ABP | 0.075 | 0.062 | 0.07 |
| VAP | 0.075 | — | — |
| CPI | 0.35 | 0.15 | 0.12 |
| Δ-cyanovaleric acid | 1.0 | — ca | 0.0 |
| Δ-cyanovaleramide | 0.5 | 0.13 ca | 0.2 |
| adipimide | 0.6 | — | — |

*all analyses expressed as percentages on a weight/volume basis, remaining component essentially adiponitrile

TABLE V

| Run No. | 1 | 2 | 3 | 4 | 5 | 6 |
|---|---|---|---|---|---|---|
| Solution Temperature (° C.) | 25 | 25 | 25 | 25 | 80 | 80 |
| Water (%) | 6 | 3 | 6 | 3 | 6 | 6 |
| Resin (%) | 1 | 2 | 2 | 1 | 1 | 2 |
| Impurity* | | | | | | |
| CPI | | | | | | |
| (a) after 0 minutes | 0.15 | 0.15 | 0.15 | 0.15 | 0.15 | 0.15 |
| (b) after 30 minutes | 0.18 | 0.17 | 0.19 | 0.17 | 0.19 | NA |
| (c) after 60 minutes | 0.18 | 0.17 | 0.18 | 0.17 | 0.17 | 0.18 |
| MAP | | | | | | |
| (a) after 0 minutes | 0.028 | 0.028 | 0.028 | 0.028 | 0.028 | 0.028 |
| (b) after 30 minutes | 0.017 | 0.024 | 0.010 | 0.026 | 0.025 | NA |
| (c) after 60 minutes | 0.016 | 0.022 | 0.007 | 0.015 | 0.026 | 0.017 |
| ABP | | | | | | |
| (a) after 0 minutes | 0.062 | 0.062 | 0.062 | 0.062 | 0.062 | 0.062 |
| (b) after 30 minutes | 0.041 | 0.056 | 0.022 | 0.058 | 0.052 | NA |
| (c) after 60 minutes | 0.038 | 0.055 | 0.000 | 0.059 | 0.046 | 0.032 |

*analyses are on a dry adiponitrile basis
NA — not available

EXAMPLE VI

With reference to Run #1 in Table VI, adiponitrile (#6) was mixed with molecular sieve powder in the quantity specified. The mixture was stirred for the time specified. The molecular sieve used in the run was a Type Y molecular sieve in the polyvalent cation form obtained from the Linde Division of Union Carbide Corporation (SK-500®). The molecular sieve was filtered off before analysis. Details of the run and the results obtained are given in Table VI. The composition of the adiponitrile is given in Table IV.

EXAMPLE VII

Using the procedure of Example VI adiponitrile was treated with a Type Y molecular sieve in the ammonia form obtained from the Linde Division of Union Carbide Corporation (SK-41®). Details of the run (Run #2) and the results obtained are given in Table VI.

EXAMPLE VIII

A sample of a Type X molecular sieve obtained from the Linde Division of Union Carbide Corporation under the trademark 13X was heated for one hour at 250° C. in an atmosphere of nitrogen. 0.25 g of the molecular sieve was then mixed with 25 ml of crude adiponitrile and stirred for 10 minutes at 110° C. The crude adiponitrile contained approximately 300 ppm of MAP and 700 ppm of ABP. The treatment with the molecular sieve reduced the MAP and ABP in the adiponitrile by 48% and 65% respectively.

TABLE IV

| Run No. | | 1 | 2 |
|---|---|---|---|
| Reaction Mixture | | | |
| Adiponitrile (ml) | | 100 | 100 |
| type | | #6 | #6 |
| Water (ml) | | 0 | 0 |
| Molecular Sieve (g) | | 1 | 1 |
| Reaction Conditions | | | |
| Temperature (° C.) | | 105 | 110 |
| Time (min.) | | 50 | 40 |
| Analysis | | | |
| MAP | before | 0.03 | 0.03 |
| | after | 0.004 | 0.008 |
| ABP | before | 0.07 | 0.07 |
| | after | 0.015 | 0.04 |
| CPI | before | 0.12 | 0.12 |
| | after | 0.12 | 0.12 |

EXAMPLE IX

To 25 ml of a crude adiponitrile manufactured from adipic acid and ammonia and containing approximately 300 ppm MAP, 700 ppm ABP and essentially 0% water was added approximately one gram of bentonite. The mixture was stirred for 10 minutes at room temperature and then analyzed by gas chromatography. Approximately 25% of the MAP and 24% of the ABP has been removed from the crude adiponitrile.

EXAMPLE X 2 ml of water was added to the above mixture. The resultant mixture was stirred for a further 25 minutes at room temperature and re-analyzed. Approximately 61% of the MAP and 51% of the ABP had been removed from the crude adiponitrile.

EXAMPLE XI

To 25 ml of a crude adiponitrile manufactured from adipic acid and ammonia and containing approximately 1200 ppm of MAP was added 2 ml of water and approximately one gram of bentonite. The mixture was stirred for 10 minutes at room temperature and then analyzed by gas chromatography. Approximately 54% of the MAP had been removed from the crude adiponitrile.

0.1 ml of 85% phosphoric acid was added to the above mixture. The resultant mixture was stirred for a further 30 minutes at room temperature. Analysis showed that 100% of the MAP had been removed from the crude adiponitrile.

EXAMPLE XII

To 25 ml of a crude adiponitrile manufactured from adipic acid and ammonia and containing approximately 300 ppm of MAP and approximately 700 ppm of ABP was added 2 ml of water and 0.074 g of boron phosphate. The mixture was stirred for 25 minutes at room temperature and then analyzed. Approximately 37% of the MAP and 73% of the ABP had been removed from the crude adiponitrile.

I claim:

1. A process for substantially reducing the level of N-heterocyclic amines in adiponitrile made from adipic acid and ammonia comprising contacting said adiponitrile essentially free of ammonia with a solid acidic sorption agent while minimizing the hydrolyses of any 2-cyanocyclopentylideneimine present in the adiponitrile, said sorption agent and temperature of contact being selected from the class consisting of (1) weak-acid cation exchange resins at 20°–140° C., (2) boron phosphate at 20°–100° C. (3) bentonite at 20°–100° C. and (4) molecular sieves at 100°–250° C. with said process being conducted in the presence of less than 0.1% by weight of water when molecular sieves comprise said sorption agent.

2. The process of claim 1 wherein the adiponitrile is contacted with sorption agents (1), (2) and (3) in the presence of water.

3. The process of claim 2 wherein the sorption agent is bentonite in the presence of phosphoric acid.

4. The process of claim 2 wherein the sorption agent is boron phosphate.

5. The process of claim 2 wherein the sorption agent is a weak acid cation exchange resin.

6. The process of claim 1 wherein the molecular sieve is a Type Y molecular sieve.

* * * * *